(12) United States Patent
Ma et al.

(10) Patent No.: US 12,734,566 B2
(45) Date of Patent: Sep. 15, 2026

(54) FIELD IN-PLACE FILM-COVERING FERMENTATION DEVICE

(71) Applicant: Institute of Applied Ecology, Chinese Academy of Sciences, Shenyang (CN)

(72) Inventors: Jian Ma, Shenyang (CN); Xin Chen, Shenyang (CN); Caiyan Lu, Shenyang (CN); Guangyu Chi, Shenyang (CN)

(73) Assignee: Institute of Applied Ecology, Chinese Academy of Sciences, Shenyang (CN)

( * ) Notice: Subject to any disclaimer, the term of this patent is extended or adjusted under 35 U.S.C. 154(b) by 813 days.

(21) Appl. No.: 18/083,508

(22) Filed: Dec. 17, 2022

(65) Prior Publication Data

US 2023/0278084 A1 Sep. 7, 2023

(30) Foreign Application Priority Data

Mar. 3, 2022 (CN) ........................ 202210203377.1

(51) Int. Cl.

| | |
|---|---|
| ***B09B 3/60*** | (2022.01) |
| ***C12M 1/00*** | (2006.01) |
| ***C12M 1/12*** | (2006.01) |
| ***C12M 1/34*** | (2006.01) |

(52) U.S. Cl.

CPC .............. *B09B 3/60* (2022.01); *C12M 25/14* (2013.01); *C12M 29/20* (2013.01); *C12M 41/12* (2013.01)

(58) Field of Classification Search

CPC ......... B09B 3/60; C12M 25/14; C12M 29/20; C12M 41/12; C12M 29/06; Y02W 30/40; C05F 17/979; C05F 17/90; C05F 17/964; C05F 17/993

See application file for complete search history.

(56) References Cited

FOREIGN PATENT DOCUMENTS

| | | | | | |
|---|---|---|---|---|---|
| CN | 105732144 | A | * | 7/2016 | ............ C05F 17/979 |
| CN | 207933303 | U | * | 10/2018 | |
| JP | 2008081354 | A | * | 4/2008 | |
| JP | 3167131 | U | * | 4/2011 | |
| KR | 20130085131 | A | * | 7/2013 | ........... C05F 17/979 |

* cited by examiner

*Primary Examiner* — Liban M Hassan
(74) *Attorney, Agent, or Firm* — Hemisphere Law, PLLC

(57) ABSTRACT

A field in-place film-covering fermentation device is provided. The device includes a support structure, a covering film, and a ventilation structure. The support structure is connected to the covering film through cross-connecting rings on the covering film to form a columnar pile structure. The covering film is in a split configuration to form an upper surface, a lower surface, and a side elevation of the columnar pile structure by cutting. The ventilation structure is fixed in the columnar pile structure. The device can realize the in-place and nearby treatment of organic wastes, improve the material conversion efficiency of agricultural organic wastes in their production area, and promote the improvement of the regional ecological environment.

10 Claims, 3 Drawing Sheets

FIELD IN-PLACE FILM-COVERING FERMENTATION DEVICE

TECHNICAL FIELD

The disclosure relates to the field of agricultural organic waste recycling, and more particularly to a field in-place film-covering fermentation device.

BACKGROUND

Aerobic composting is a process in which aerobic bacteria can degrade organic wastes to produce finished organic fertilizer through oxidation, decomposition and absorption of organic substances under conditions of good ventilation and sufficient oxygen, and it is also a main way for recycling agricultural organic wastes. Static pile composting, dynamic pile composting and reactor composting are common methods of the aerobic composting, which have been widely used, and have formed a composting site mode for centralized treatment of the agricultural organic wastes with composting sites as the core, which is also the main direction of composting industry development. The composting site mode for treating the agricultural organic wastes has the advantages of large processing capacity, easy process regulation, and the like. In addition, the large fermentation pile (more than 100 cubic meters abbreviated as $m^3$) has a strong buffer capacity for heat, moisture, microorganisms, and the like in the composting process, and it is easier to achieve rapid composting of different organic materials.

Although the centralized treatment mode of composting site has solved the treatment problems of most agricultural organic wastes, due to the influence of factors such as high collection, storage and transportation costs, high capital construction costs, low investment income ratio, and so on, there are few organic fertilizer enterprises have interest in raw materials from decentralized sources, such as decentralized farmland straws, decentralized livestock and poultry manure, and facility tail vegetables, which makes the treatment of such agricultural organic wastes become a blind spot for aerobic composting, greatly limits the efficiency of material circulation transformation in regional agricultural ecosystems, and also becomes the main obstacle to the improvement of rural ecological environment in related areas.

Moreover, due to the limitation of the local total amount of the decentralized organic materials and the difficulty in collection, the fermentation pile is often small during the composting treatment of decentralized agricultural organic wastes, it is difficult to maintain the temperature of the pile and regulate the moisture during the fermentation process, and the regulatory redundancy is small. There is a high probability that the composting will fail and the quality of the composting products will be poor.

SUMMARY

To solve the above technical problems, embodiments of the disclosure are implemented as follows.

Specifically, a field in-place film-covering fermentation device provided by the embodiments of the disclosure includes: a support structure, a covering film, and a ventilation structure. The support structure is connected to the covering film through cross-connecting rings on the covering film to form a columnar pile structure. The covering film is in a split configuration to form an upper surface, a lower surface, and a side elevation of the columnar pile structure by cutting. The ventilation structure is fixed in the columnar pile structure.

In an embodiment, the support structure is composed of wire mesh, two ends of the wire mesh are welded with metal plates, and the metal plates are disposed with blocking leakage mechanisms to make the wire mesh be erected in a cylindrical shape through connection of the blocking leakage mechanisms on the metal plates.

In an embodiment, the covering film is made of polytetrafluoroethylene material having a microporous structure with a pore size of 0.2 micrometers (μm).

In an embodiment, the ventilation structure comprises a non-power wind cap, an electric air valve, a perforated polyvinyl chloride (PVC) pipe, a temperature sensing probe, a solar power supply unit and a control circuit; the non-power wind cap, the electric air valve and the perforated PVC pipe are sequentially connected in that order, the temperature sensing probe is disposed inside the columnar pile structure; and the control circuit is individually connected to the solar power supply unit, the temperature sensing probe and the electric air valve.

In an embodiment, the non-power wind cap, the electric air valve and the perforated PVC pipe are placed vertically above the columnar pile structure.

In an embodiment, a pipe diameter of the perforated PVC pipe is determined by a formula as follows:

$$R_{pipe} = 0.5 \times \sqrt{\frac{S_{structure} \times K_{gas} \times P_{material}}{\pi \times V_{interal\ max}}};$$

where $R_{pipe}$ represents a radius of the perforated PVC pipe, $S_{structure}$ represents a ventilation area of the covering film formed on a pile body, $K_{gas}$ represents a maximum permeability of the covering film used, $P_{material}$ represents a porosity of a material to be composted, and $V_{interal\ max}$ represents a maximum internal wind speed generated by rotation of the non-power wind cap by an external wind pressure without considering an internal heat pressure.

In an embodiment, a number of holes of the perforated PVC pipe is determined by $$n = \frac{S_{pipe}}{S_{hole}},$$

where $S_{pipe}$ represents a cross-sectional area of the perforated PVC pipe, $S_{hole}$ represents a perforated area of the perforated PVC pipe, and a radius r of $S_{hole}$ is in a range of 10 millimeters (mm) to 30 mm.

In an embodiment, a perforated range of the perforated PVC pipe is from a bottom of the perforated PVC pipe to a lower edge of a rotating circumference of the electric air valve, and a longitudinal spacing of the perforated PVC pipe is determined by $$d_{hole} = \frac{L_{material}}{4n},$$

where $L_{material}$ represents a length from the electric air valve to the bottom of the perforated PVC pipe.

In an embodiment, a height h of the support structure is in a range of greater than 1 meter and less than or equal to 2 in.

In an embodiment, the control circuit is configured to control opening of the electric air valve, the temperature sensing probe is configured to measure temperature of a pile body in the columnar pile structure, and relationships between the temperature of the pile body and the opening of the electric air valve are as follows:

| Pile temperature (t° C.) | Air valve opening (%) |
|---|---|
| 0 < t ≤ 15 | 10 |
| 15 < t ≤ 35 | 20 |
| 15 < t ≤ 35 | 40 |
| 35 < t ≤ 60 | 60 |
| t > 60 | 100 |

At least one of the above technical solutions adopted in the embodiments of the disclosure can achieve the following beneficial effects.

The disclosure proposes the field in-place film-covering fermentation device, which can realize the efficient composting treatment of decentralized and small amount of agricultural organic wastes in the field. By using the device of the disclosure, the organic wastes can be treated in-place nearby, the material conversion efficiency of the agricultural organic wastes in the production area is improved, and the regional ecological environment is improved.

The device provided by the disclosure adopts a principle of chimney action to change the original forced air blowing oxygen supply mode into passive air suction oxygen supply mode, which can realize high-standard aerobic composting in the field with high efficiency and low cost, thereby greatly reducing the storage and transportation cost and improving the decentralized composting quality.

After using the device, the composting of the agricultural organic wastes can be realized under the condition of no external power, the composting time can be shortened to about 28 days from 1-3 months in the field, and the low-cost operation can be realized while the quality of the composting meets the requirements of relevant standards.

BRIEF DESCRIPTION OF DRAWINGS

The brief description of drawings herein is used to provide a further understanding of the disclosure and form a part of the disclosure. The illustrated embodiments and their descriptions of the disclosure are used to explain the disclosure, and do not constitute improper limitations of the disclosure.

Figure 1A:
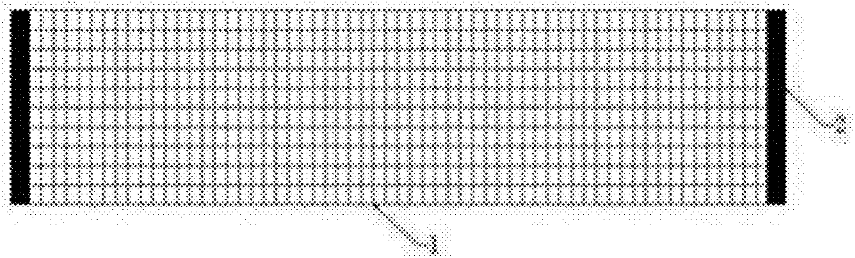
FIGS. 1A-1C illustrate schematic views showing a support structure and a covering film of a field in-place film-covering fermentation device of the disclosure.

Description of reference numerals: 1. wire mesh; 2. metal plate; 3. blocking leakage mechanism; 4. cross-connecting ring; 5. covering film; 6. VELCRO® fastener; 7. upper surface; 8. upper surface VELCRO® fastener; 9. upper surface support rod; 10. reserved mounting hole for ventilation structure; 11. lower surface; 12. pin-reserved hole; 13. lower surface VELCRO® fastener; 14. non-power wind cap; 15. perforated polyvinyl chloride (PVC) pipe; 16. electric air valve; 17. hole; 18. fixing pins; 19. solar panel; 20. support rod; 21. control box (including a control circuit 211, a battery 212); 22. electric air valve control line; 23. temperature sensing probe.

DETAILED DESCRIPTION OF EMBODIMENTS

In order to make purposes, technical solutions, and advantages of the disclosure clearer, the technical solution of the disclosure will be described clearly and completely in combination with the specific embodiments of the disclosure and the corresponding drawings. Apparently, the described embodiments are only part of the embodiments of the disclosure, not all of them. Based on the embodiments in the disclosure, all other embodiments obtained by those skilled in the art without paying creative work fall within the scope of protection in the disclosure.

The following describes in detail The technical solutions provided by embodiments of the disclosure are described in detail below with reference to the accompanying drawings.

The disclosure provides a field in-place film-covering fermentation device, including a support structure, a covering film 5, and a ventilation structure. The support structure and the covering film are connected through cross-connecting rings 4 on the covering film 5 to form a columnar pile structure. The ventilation structure is fixed in a columnar pile structure (also referred to as a columnar reactor structure). A circumference interval between the ventilation structure and a boundary of the columnar pile structure or between different ventilation structures is in a range of 0.7 meters (m)$<d_{structure}\leq$1 m.

Figure 1B:
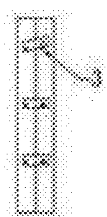
Figure 1C:
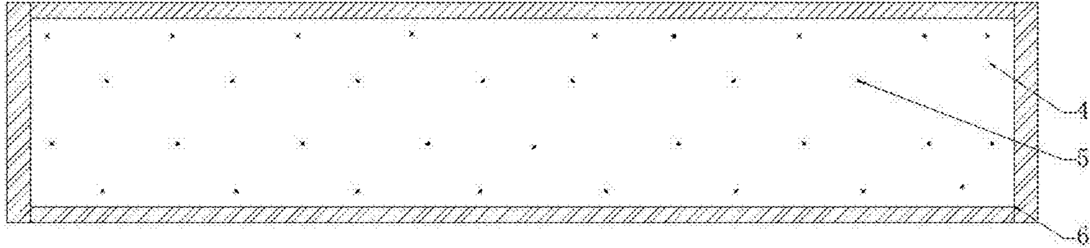

FIGS. 1A-1C shows the support structure and the covering film of the field in-place film-covering fermentation device of the disclosure, as shown in FIGS. 1A-1C, the support structure is composed of a wire mesh 1, two ends of the wire mesh 1 are welded with metal plates 2, and the metal plates 2 are disposed with blocking leakage mechanisms 3, the wire mesh 1 is erected in a cylindrical shape through the connection of the blocking leakage mechanisms 3 on the metal plates 2 to form a support structure of a columnar pile body to thereby support a fermentation pile body, and a height h of the formed support structure is in a range of greater than 1 in and less than or equal to 2 in (i.e., 1 m<h≤2 m).

Figure 2A:
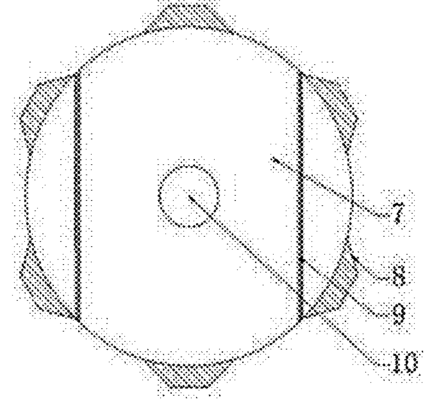
FIGS. 2A-2B illustrate schematic views showing upper and lower surfaces of the covering film on a pile body of the field in-place film-covering fermentation device of the disclosure.
Figure 2B:
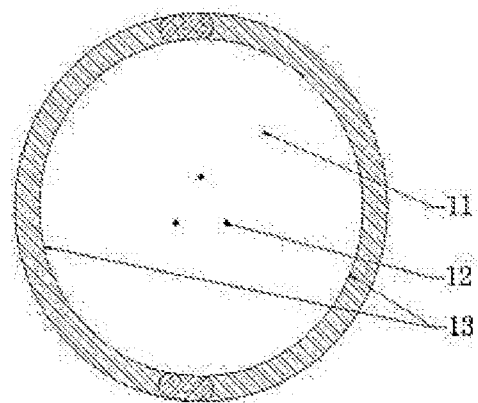

As shown in FIGS. 1A-1C and FIGS. 2A-2B, the covering film 5 is in a split configuration to form an upper surface 7 (as shown in FIG. 2A), a lower surface 11 (as shown in FIG. 2B) and a side elevation (as shown in FIG. 1C) of the columnar pile structure by cutting, and the three surfaces are connected by VELCRO® fasteners 6.

As shown in FIG. 2A, an edge of the upper surface 7 of the covering film 5 is disposed with upper surface VELCRO® fasteners 8 spaced with each other, and the upper surface 7 of the covering film 5 is supported by upper surface support rods 9. Specifically, the upper surface support rods 9 may be multiple and may be symmetrically arranged. A center of the upper surface 7 of the covering film 5 is defined with a through hole as a reserved mounting hole 10 for the installation of the ventilation structure.

As shown in FIG. 2B, an edge of the lower surface 11 of the covering film 5 is disposed with lower surface VELCRO® fasteners 8 spaced with each other. A center of the lower surface 11 of the covering film 5 is defined with pin-reserved holes 12 for the fixing of fixing pins 18 (as shown in FIG. 3).

The covering film 5 is made of polytetrafluoroethylene material, specifically expanded polytetrafluoroethylene (ePTFE) material, having a microporous structure with a pore size of 0.2 micrometers (μm), which can realize effective physical isolation of dust, aerosols, and microorganisms.

Figure 3:
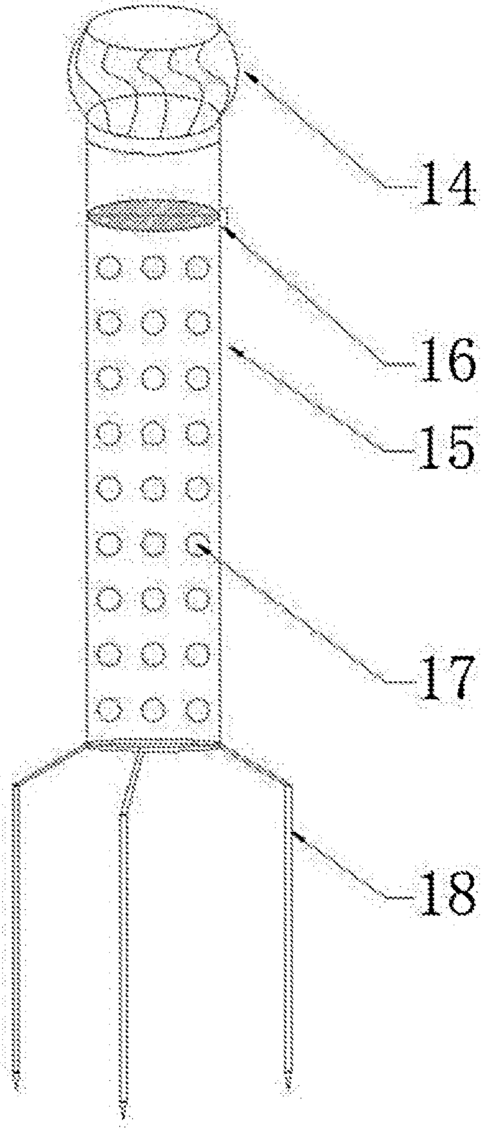
FIG. 3 illustrates a schematic view showing a ventilation structure of the field in-place film-covering fermentation device of the disclosure.
Figure 4A:
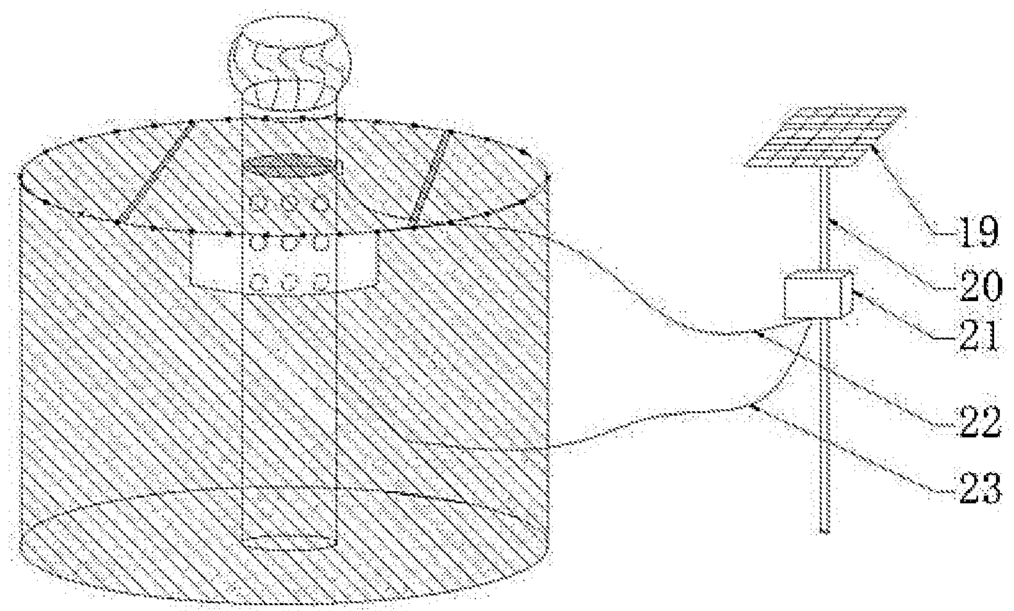
FIG. 4A illustrates a schematic view showing a general layout of the field in-place film-covering fermentation device of the disclosure.
Figure 4B:
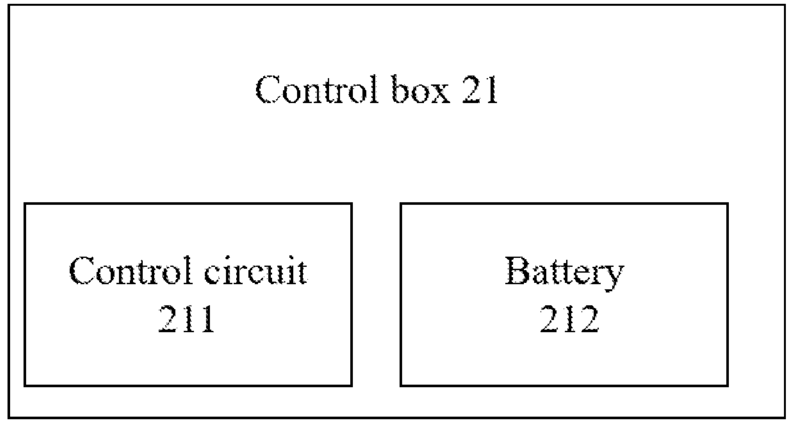
FIG. 4B illustrates a schematic view showing a control box of the field in-place film-covering fermentation device of the disclosure.

As shown in FIG. 3 and FIGS. 4A-4B, the ventilation structure includes: a non-power wind cap 14 (also referred to as air turbine vent 14), an electric air valve 16, a perforated polyvinyl chloride (PVC) pipe 15, a temperature sensing probe 23, a solar power supply unit 19 (also referred to as a solar panel 19) and a control box 21 (including a control circuit 211 and a battery 212). The non-power wind cap 14, the electric air valve 16 and the perforated PVC pipe 15 are connected sequentially in that order, and the temperature sensing probe 23 is disposed inside the columnar pile structure. The control circuit 211 is individually connected to the solar panel 19, the temperature sensing probe 23 and the electric air valve 16.

The ventilation structure further includes the fixing pins 18 used to fix the perforated PVC pipe 15. There are three fixing pins 18, forming a tripod support (also referred to as trishores).

As shown in FIGS. 4A-4B, the solar panel 19 is supported by a support rod 20, and the control circuit 211 controls the electric air valve 16 through an electric air valve control line 22.

A diameter of the perforated PVC pipe 15 is determined by parameters such as air permeability of the covering film area of the formed pile structure in unit volume, porosity of the fermentation material to be composted and the like, specifically, the diameter is determined by the following formula:

$$R_{pipe} = 0.5 \times \sqrt{\frac{S_{structure} \times K_{gas} \times P_{material}}{\pi \times V_{interal\ max}}};$$

where $R_{pipe}$ represents a radius of the perforated PVC pipe, $S_{structure}$ represents a ventilation area of the covering film formed on the pile body, $K_{gas}$ represents a maximum permeability of the covering film used, $P_{material}$ represents a porosity of a material to be composted, and $V_{interal\ max}$ represents a maximum internal wind speed generated by rotation of the non-power wind cap by an external wind pressure without considering an internal heat pressure. Generally, the value of $V_{interal\ max}$ is determined when the external wind speed is 10 meters per second (m/s), usually 0.1-0.14 m/s.

Holes 17 of four rows in the perforated PVC pipe 15 form 90° to each other, and the number of holes 17 is determined by $$n = \frac{S_{pipe}}{S_{hole}},$$

where $S_{pipe}$ represents a cross-sectional area of the perforated PVC pipe, $S_{hole}$ represents a perforated area of the perforated PVC pipe, and a radius r of $S_{hole}$ is in a range of 10 millimeters (mm) to 30 mm A perforated range of the perforated PVC pipe is from a bottom of the perforated PVC pipe to a lower edge of a rotating circumference of the electric air valve, and a longitudinal spacing of the holes is determined by $$d_{hole} = \frac{L_{material}}{4n}$$

after the number of holes 17 is determined, where $d_{hole}$ represents the longitudinal spacing of the perforated PVC pipe, $L_{material}$ represents a length from the electric air valve to the bottom of the perforated PVC pipe, and $L_{material}$ is also a maximum cumulative height of compost materials.

The control circuit 211 is used to control opening of the electric air valve, and the temperature sensing probe 23 is used to measure temperature of the pile body in the columnar pile structure. A relationship between the temperature of the pile body and the opening of the electric air valve is as follows:

| Pile temperature (t° C.) | Air valve opening (%) |
|---|---|
| 0 < t ≤ 15 | 10 |
| 15 < t ≤ 35 | 20 |
| 15 < t ≤ 35 | 40 |
| 35 < t ≤ 60 | 60 |
| t > 60 | 100 |

The disclosure proposes the field in-place film-covering fermentation device, which can realize the efficient composting treatment of decentralized and small amount of agricultural organic wastes in the field. By using the device of the disclosure, the organic wastes can be treated in-place nearby, the material conversion efficiency of the agricultural organic wastes in the production area is improved, and the regional ecological environment is improved. The device provided by the disclosure can realize high-standard aerobic composting in the field with high efficiency and low cost, thereby greatly reducing the storage and transportation cost and improving the decentralized composting quality.

After using the device, the composting of the agricultural organic wastes can be realized under the condition of no external power, the composting time can be shortened to about 28 days from 1-3 months in the field, and the low-cost operation can be realized while the quality of the composting meets the requirements of relevant standards.

It should also be noted that the terms “including”, “comprising” or any other variant thereof are intended to cover a non-exclusive inclusion, such that an apparatus including a series of elements not only includes those elements, but also includes other elements not explicitly listed, or also includes elements inherent to such apparatus. Without further restrictions, the elements defined by the statement “including one . . . ” do not exclude the existence of other identical elements in the apparatus including the elements.

Each embodiment in the disclosure is described in a progressive manner, the same and similar parts of each embodiment can be referred to each other, and each embodiment focuses on the differences with other embodiments. In particular, for a system embodiment, since it is basically similar to a method embodiment, the description is relatively simple, and the relevant part can be referred to the description of the method embodiment.

The above is only the illustrated embodiment of the disclosure and is not intended to limit the disclosure. For those skilled in the art, the disclosure may have various changes and variations. Any modification, equivalent replacement, improvement, etc. made within the spirit and principle of this disclosure shall be included in the scope of claims of this disclosure.

What is claimed is:

1. A field in-place film-covering fermentation device, comprising a support structure, a covering film and a ventilation structure;

wherein the support structure is composed of wire mesh, two ends of the wire mesh are welded with metal plates, and the metal plates are connected to each other by blocking leakage to make the wire mesh be erected in a cylindrical shape;

the covering film is pre-divided into three separable segments comprising an upper surface segment, a lower surface segment, and a side elevation segment; and the three separable segments are configured to collectively wrap around the support structure to form a columnar enclosure enclosing a compost material;

the support structure is connected to the covering film through cross-connecting rings on the covering film to form a columnar pile structure, and adjacent edges of the three separable segments are connected to each other via fasteners; and the ventilation structure is fixed in the columnar pile structure.

2. The field in-place film-covering fermentation device according to claim 1, wherein the covering film is made of polytetrafluoroethylene material having a microporous structure with a pore size of 0.2 micrometers (um).

3. The field in-place film-covering fermentation device according to claim 1, wherein the ventilation structure comprises a non-power wind cap, an electric air valve, a perforated polyvinyl chloride (PVC) pipe, a temperature sensing probe, and a control circuit; the non-power wind cap, the electric air valve and the perforated PVC pipe are sequentially connected in that order, the temperature sensing probe is disposed inside the columnar pile structure; and the control circuit is individually connected to the temperature sensing probe and the electric air valve.

4. The field in-place film-covering fermentation device according to claim 3, wherein the non-power wind cap, the electric air valve and the perforated PVC pipe are placed vertically above the columnar pile structure.

5. The field in-place film-covering fermentation device according to claim 3, wherein a pipe diameter of the perforated PVC pipe is determined by a formula as follows:

$$R_{pipe} = 0.5 \times \sqrt{\frac{S_{structure} \times K_{gas} \times P_{material}}{\pi \times V_{interal\ max}}},$$

where $R_{pipe}$ represents a radius of the perforated PVC pipe, $S_{structure}$ represents a ventilation area of the covering film formed on a pile body, $K_{gas}$ represents a maximum permeability of the covering film used, $P_{material}$ represents a porosity of a material to be composted, and $V_{interal\ max}$ represents a maximum internal wind speed generated by rotation of the non-power wind cap caused by an external wind pressure without considering an internal heat pressure.

6. The field in-place film-covering fermentation device according to claim 5, wherein a number of holes of the perforated PVC pipe is determined by $$d_{hole} = \frac{L_{material}}{4n},$$

where $S_{pipe}$ represents a cross-sectional area of the perforated PVC pipe, $S_{hole}$ represents a perforated area of the perforated PVC pipe, and a radius r of $S_{hole}$ is in a range of 10 millimeters (mm) to 30 mm.

7. The field in-place film-covering fermentation device according to claim 6, wherein a perforated range of the perforated PVC pipe is from a bottom of the perforated PVC pipe to a lower edge of a rotating circumference of the electric air valve, and a longitudinal spacing of the perforated PVC pipe is determined by $$n = \frac{S_{pipe}}{S_{hole}},$$

where $d_{hole}$ represents the longitudinal spacing of the perforated PVC pipe and $L_{material}$ represents a length from the electric air valve to the bottom of the perforated PVC pipe.

8. The field in-place film-covering fermentation device according to claim 3, wherein the control circuit is configured to control opening of the electric air valve, the temperature sensing probe is configured to measure temperature of a pile body in the columnar pile structure, and relationships between the temperature of the pile body and the opening of the electric air valve are as follows:

10% of opening of the electric air valve corresponding to the temperature t of the pile body being greater than 0° C. and less than or equal to 15° C.;

20% of opening of the electric air valve and 40% of opening of the electric air valve both corresponding to the temperature t of the pile body being greater than 15° C. and less than or equal to 35° C.;

60% of opening of the electric air valve corresponding to the temperature t of the pile body being greater than 35° C. and less than or equal to 60° C.; and 100% of opening of the electric air valve corresponding to the temperature t of the pile body being greater than 60° C.

9. The field in-place film-covering fermentation device according to claim 3, wherein a height h of the support structure is in a range of greater than 1 meter and less than or equal to 2 m.

10. A field in-place film-covering fermentation device, comprising:

a support structure comprising a cylindrical wire mesh and metal plates fixedly attached to opposite ends of the wire mesh;

a covering film, wherein the covering film is pre-divided into three separable segments consisting of an upper surface segment, a lower surface segment, and a side elevation segment, wherein the three segments are configured to collectively wrap around the support structure to form a columnar enclosure enclosing a compost material; and the support structure is connected to the covering film through cross-connecting rings on the covering film to form a columnar pile structure;

fasteners, configured to releasably connect adjacent edges of the three segments to one another, thereby forming a sealed enclosure around the support structure; and a ventilation structure, comprising a non-power wind cap, an electric air valve, a perforated perforated polyvinyl chloride (PVC) pipe, a temperature sensing probe, and a control circuit; wherein the non-power wind cap, the electric air valve and the perforated PVC pipe are sequentially connected in that order and placed vertically above the columnar pile structure, the temperature sensing probe is disposed inside the columnar pile structure; and the control circuit is individually connected to the temperature sensing probe and the electric air valve, such that a chimney effect is generated to passively draw air through the compost material without any external power source.

* * * * *